United States Patent [19]

Hardt et al.

[11] Patent Number: 5,286,874
[45] Date of Patent: Feb. 15, 1994

[54] PROCESS FOR THE PRODUCTION OF BISMALEINIMIDE DERIVATIVES

[75] Inventors: Peter Hardt, Visp; Theodor Völker, Reinach, both of

[73] Assignee: Lonza Ltd., Gampel/Valais, Switzerland

[21] Appl. No.: 981,060

[22] Filed: Nov. 24, 1992

[30] Foreign Application Priority Data

Nov. 28, 1991 [CH] Switzerland .................. 3486/91

[51] Int. Cl.⁵ .......................................... C07D 207/24
[52] U.S. Cl. ................................................ 548/522
[58] Field of Search ................................... 548/522

[56] References Cited

FOREIGN PATENT DOCUMENTS

| | | | |
|---|---|---|---|
| 334497 | 2/1989 | European Pat. Off. | 548/522 |
| 393713 | 4/1990 | European Pat. Off. | 548/522 |
| 387381 | 9/1990 | European Pat. Off. | 548/522 |
| 544266 | 2/1993 | European Pat. Off. | 548/522 |
| 57-159764 | 10/1982 | Japan | 548/522 |
| 61-093159 | 5/1986 | Japan | 548/522 |
| 2-58267 | 12/1990 | Japan | 548/522 |
| 2043054 | 10/1980 | United Kingdom | 548/522 |

OTHER PUBLICATIONS

Patent Abstracts of Japan, vol. 10. No. 269 (C-372) (2325), (Sep. 1986).
Patent Abstracts of Japan, vol. 7, No. 3, (C-143), (1148), (Jan. 7, 1983).

*Primary Examiner*—Mary C. Lee
*Assistant Examiner*—Joseph K. McKane
*Attorney, Agent, or Firm*—Fisher, Christen & Sabol

[57] ABSTRACT

A process for the production of bismaleinimide derivatives of the formula:

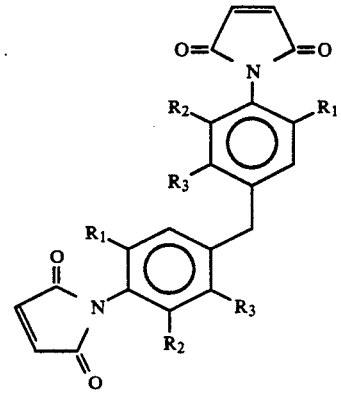

In the first step, maleic acid anhydride of the formula:

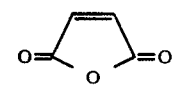

is converted with a methyl-bis-aniline of the formula:

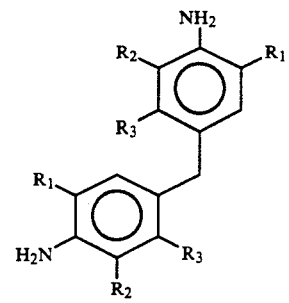

in an unhalogenated aromatic hydrocarbon as the solvent, into the corresponding amide acid. In the second step, the amide acid is converted, without isolation, in the presence of an acid catalyst, into the end product of the formula I.

10 Claims, No Drawings

PROCESS FOR THE PRODUCTION OF BISMALEINIMIDE DERIVATIVES

BACKGROUND OF THE INVENTION

1. Field of the Invention

The invention relates to a process for the production of bismaleinimide derivatives of the formula:

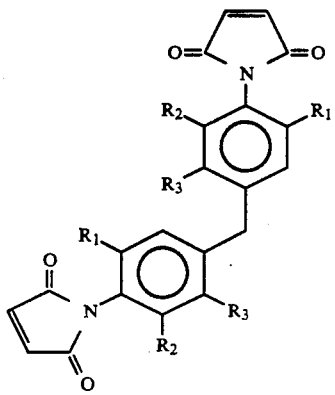

wherein $R_1$ and $R_2$ are the same or different and each is a $C_1$–$C_4$-alkyl group, branched or unbranched, and $R_3$ is a halogen or hydrogen atom starting from maleic acid anhydride and a methylene-bis-aniline.

2. Background Art

The bismaleinimide derivatives of formula I are used, for example, for the production of heat-resistant bismaleinimide resins (Japanese Laid-Open Patent Application No. 61-093159).

A known embodiment for the production of bismaleinimide derivatives is described, for example, in Japanese Laid-Open Patent Application No. 57-159764 (Japanese Patent No. 02-058267). In the process, a methylenebis[N-(monoalkyl)-phenylene]maleinimide] is produced, starting from maleic acid anhydride and a methylene-bis-aniline, in the presence of an acid catalyst. To obtain a pure product with a good yield, a mixture of a halogenated hydrocarbon with an aprotic polar solvent is necessarily used in the process as the solvent. From Comparison Example 2 (page 10) of the above-mentioned application it is known that, if dichloroethane is replaced by toluene in the solvent mixture, both the purity is reduced from 93 to 67 percent and the yield of the desired end product is also reduced from 95 to 88 percent. The substitution of dichloroethane by xylene even reduces both the purity from 95 to 53 percent and the yield of the desired end product from 95 to 64 percent. A major drawback of the process lies in that the environmentally polluting halogenated hydrocarbons have to be used as the solvent in order to obtain a pure end product in a good yield.

BROAD DESCRIPTION OF THE INVENTION

The main objective of the invention is to eliminate such drawback and to provide an ecological process for the production of bismaleinimide derivatives. Other objectives and advantages of the invention are set out herein or are obvious herefrom to one skilled in the art.

The objectives and advantages of the invention are achieved by the process according to the invention.

The invention involves a process for the production of bismaleinimide derivatives of the formula:

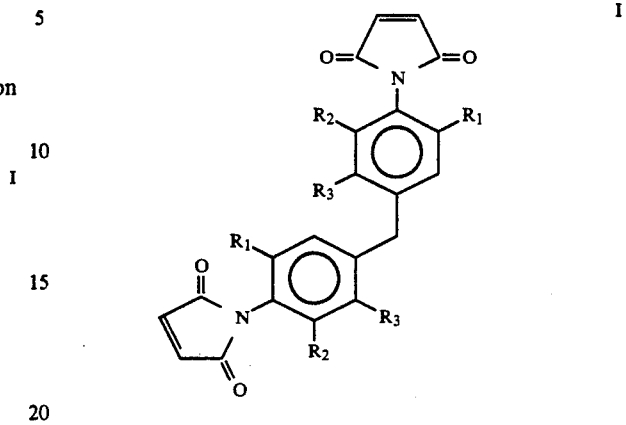

wherein $R_1$ and $R_2$ are the same or different and each is a $C_1$–$C_4$-alkyl group, branched or unbranched, and $R_3$ is a halogen or hydrogen atom. In the first step, maleic acid anhydride of the formula:

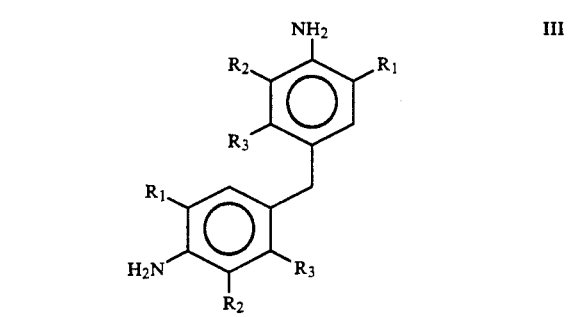

is converted with a methylene-bis aniline of the general formula:

wherein $R_1$, $R_2$ and $R_3$ have the above-mentioned meanings, in an unhalogenated aromatic hydrocarbon as the solvent, into the corresponding amide acid. The amide acid is converted, without isolation, in the second step, in the presence of an acid catalyst into the end product according to the general formula I.

Preferably in the first step, 4,4'-methylenebis[(2-ethyl-6-methyl)aniline], 4,4'-methylenebis[(2,6-diethyl)aniline], 4,4'-methylenebis[(2-isopropyl-6-methyl)aniline], 4,4'-methylenebis[(2,6-diisopropyl)aniline] or 4,4'-methylenebis[(3-chloro-2,6-diethyl)aniline] is used as the methylene-bis-aniline. Preferably the reaction in the first step takes place at a temperature from 20° to 140° C. Preferably in the second step, p-toluenesulfonic acid or its hydrate is used as the acid catalyst. Preferably the reaction in the second step takes place at a temperature of from 90° C. to the reflux temperature. Preferably, in the first and second steps toluene or xylene isomers are used as the unhalogenated aromatic hydrocarbon.

DETAILED DESCRIPTION OF THE INVENTION

According to the invention, the process is performed so that in the first step maleic acid anhydride of the formula:

II is converted with a methylene-bis-aniline of the general formula:

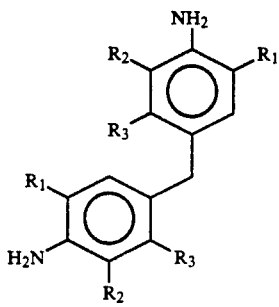
III wherein $R_1$, $R_2$ and $R_3$ have the above-mentioned meanings, in an unhalogenated aromatic hydrocarbon as solvent, into the corresponding amide acid. The amide acid is converted, without isolation, in the second step, in the presence of an acid catalyst, into the end product according to the general formula I.

The reaction in the first step suitably takes place with a methylene-bis-aniline, in which
$R_1=R_2=$ methyl, ethyl or isopropyl and
$R_3$ is a hydrogen atom,
or
$R_1=R_2=$ methyl, ethyl or isopropyl and
$R_3$ is a chlorine atom,
or
$R_1=$ methyl, $R_2=$ ethyl or isopropyl and
$R_3$ is a hydrogen atom,
or
$R_1$ is ethyl, $R_2$ is isopropyl and
$R_3$ is a hydrogen atom.
Preferably as the methylene-bis-aniline in the first step, 4,4'-methylenebis[(2-ethyl-6-methyl)aniline] ($R_1=CH_3$, $R_2=C_2H_5$, $R_3=H$), 4,4'-methylenebis[(2,6-diethyl)aniline] ($R_1=R_2=C_2H_5$, $R_3=H$), 4,4'-methylenebis[(2-isopropyl-6-methyl)aniline] ($R_1=$ isopropyl, $R_2=CH_3$, $R_3=H$), 4,4' -methylenebis[(3-chloro-2,6-diethyl)aniline] ($R_1=R_2=C_2H_5$, $R_3=Cl$) or 4,4'-methylenebis[(2,6-diisopropyl)aniline] ($R_1=R_2=$ isopropyl, $R_3=H$) is used.

Suitably the reaction in the first step is performed stoichiometrically with 2 mol of the maleic acid anhydride, optionally in a light excess, relative to 1 mol of the methylene-bis-aniline. The reaction in the first step takes place suitably at temperatures of 20° to 140° C., preferably of 70° to 90° C.

As the solvent in the first and second steps, unhalogenated aromatic hydrocarbons are used. Suitably toluene, xylene isomers, mixtures of toluene and xylene isomers, ethyl benzene, cumen or cymene isomers, preferably xylene isomers or toluene, are used as solvent.

After the first reaction step, the acid catalyst is then directly added to the amide acid formed in the first step. Suitably the acid catalyst is used in an amount of 0.01 to 0.3 mol, preferably of 0.05 to 0.1 mol, per mole of maleic acid anhydride. As the acid catalysts, for example, p-toluenesulfonic acid, methanesulfonic acid, benzenesulfonic acid or their hydrates can be used. Preferably p-toluenesulfonic acid monohydrate is used.

The reaction in the second step is suitably performed up to the reflux temperature of the solvent or solvent mixture in the range of between 90° and 140° C., preferably at reflux temperature. After a usual reaction time of 0.5 to 4 hours the bismaleinimide derivative of formula I is then isolated in the usual way known in the art. Suitably the reaction time and the temperature in the second step is selected so that the reaction water formed with the described solvent is removed by azeotropic distillation.

EXAMPLE 1

4,4'-Methylenebis[N-(2-ethyl-6-methyl-1,4-phenylene)-maleinimide]

In a 2.5 l-reaction vessel with a water separator, stirrer, thermometer, reflux condenser and dropping funnel, 750 ml of xylene and 53.9 g of maleic acid anhydride (0.55 mol) were heated to 80° C. and mixed during 30 minutes with 70.6 g of 4,4'-methylenebis[(2-ethyl-6-methyl)aniline] (0.25 mol) in 250 ml of xylene. After a 60 minutes secondary reaction, 9.51 g of p-toluenesulfonic acid-monohydrate (0.05 mol) was added and the reaction content was heated to reflux temperature. After 30 to 50 minutes, 8 ml of aqueous phase had separated out in the water separator. It was allowed to react for 60 minutes more and to cool to 20° C.; it washed with sodium bicarbonate solution and the solvent was removed from the separated organic phase by vacuum distillation. The distillation residue was recrystallized from butanol. The yield was 101.5 g of 4,4'-methylenebis[N-(2-ethyl-6-methyl-1,4-phenylene)-maleinimide]. The content was 99.2 percent (HPLC) corresponding to a yield of 91.7 percent, relative to the 4,4'-methylenebis[N-(2-ethyl-6-methyl)aniline]. The melting point of the product was 164° to 165° C. Other data concerning this product was:

$^1$H-NMR (CDCl$_3$, 300 MHz) δ in ppm: 7.02 (s, 2H); 6.98 (s, 2H);
6.87 (s, 4H); 3.93 (s, 2H);
2.39 (q, 4H); 1.11 (t, 6H);
2.07 (s, 6H, J=7.6 Hz).

EXAMPLES 2 to 5

The following bismaleinimide derivatives were produced analogous to Example 1 from the corresponding methylenebisanilines:

EXAMPLE 2

4,4'-Methylenebis[N-(2,6-diethyl-1,4-phenylene)-maleinimide]

The yield was 85 percent relative to the methylenebisaniline used. The melting point of the product was 165° to 166° C. Other data concerning the product was:

$^1$H-NMR (CDCl$_3$, 300 MHz) δ in ppm: 7.04 (s, 4H); 6.84 (s, 4H);
3.99 (s, 2H); 2.38 (q, 8H);
1.11 (t, 12H);
$J$CH2,CH3=7.6 Hz

EXAMPLE 3

4,4'-Methylenebis[N-(2-isopropyl-6-methyl-1,4-phenylene)maleinimide]

The yield of the product was 88 percent relative to the methylenebisaniline used. The melting point of the product was 195° to 197° C. Other data concerning the product was:

$^1$H-NMR (CDCl$_3$, 300 MHz) δ in ppm: 7.09 (s, 2H); 6.96 (s, 2H);
6.86 (s, 4H); 3.97 (s 2H); 2.65 (sept, 2H); 1.15 (d, 12H); 2.06 (s, 6H). $J$CH,CH3 = 6.9 Hz

EXAMPLE 4

4,4'-Methylenebis[N-(3-chloro-2,6-diethyl-1,4-phenylene)maleinimide]

The yield of the product was 95 percent relative to the methylenebisaniline used. The melting point of the product was 185° to 187° C. Other data concerning the product was:

$^1$H-NMR (CDCl$_3$, 300 MHz) δ in ppm: 6.90 (s, 2H); 6.88 (s, 4H);
4.26 (s, 2H); 2.61 (q, 4H);
1.09 (t, 6H); 2.31 (q, 4H);
1.04 (t, 6H).
$J$CH2,CH3 = 7.6 Hz

EXAMPLE 5

4,4'-Methylenebis[N-(2,6-diisopropyl-1,4-phenylene)-maleinimide]

The yield of the product was 76 percent relative to the methylenebisaniline used. The melting point of the product was 216° to 218° C. Other data concerning the product was:

$^1$H-NMR (CDCl$_3$, 300 MHz) δ in ppm: 7.06 (s, 4H); 6.87 (s, 4H);
4.07 (s, 4H); 2.60 (sept. 4H);
1.13 (d, 24.
$J$CH,CH3 = 6.9 Hz

What is claimed is:

1. A process for the production of a bismaleinimide derivative of formula:

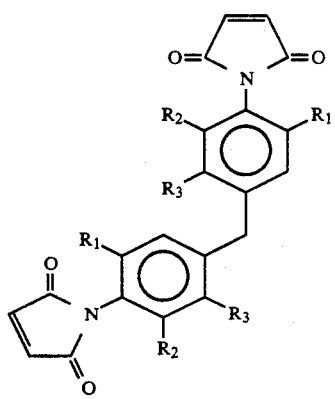

wherein R$_1$ and R$_2$ are the same or different and each is a C$_1$–C$_4$-alkyl group, branched or unbranched and R$_3$ is a halogen or hydrogen atom, characterized in that, in a first step, maleic acid anhydride of formula:

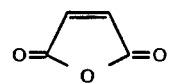

is converted with a methylene-bis-aniline of formula:

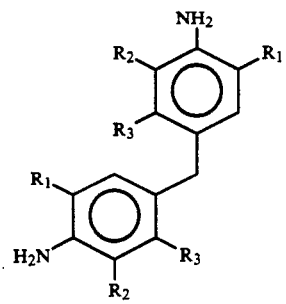

wherein R$_1$, R$_2$ and R$_3$ have the above-mentioned meanings, in an unhalogenated aromatic hydrocarbon as solvent, into the corresponding amide acid and, in a second step, the amide acid is converted, without isolation, in the presence of an acid catalyst into the end product according to general formula I.

2. The process according to claim 1 wherein, in the first step, 4,4'-methylenebis[(2-ethyl-6-methyl)aniline], 4,4'-methylenebis[(2,6-diethyl)aniline], 4,4'-methylenebis[(2-isopropyl-6-methyl)aniline], 4,4'-methylenebis[(2,6-diisopropyl)aniline] or 4,4'-methylenebis[(3-chloro-2,6-diethyl)aniline] is used as the methylene-bis-aniline.

3. The process according to claim 2 wherein the reaction in the first step takes place at a temperature from 20° to 140° C.

4. The process according to claim 3 wherein, in the second step, p-toluenesulfonic acid or its hydrate is used as the acid catalyst.

5. The process according to claim 4 wherein the reaction in the second step takes place at a temperature of from 90° C. to reflux temperature.

6. The process according to claim 5 wherein, in the first and second steps, toluene or xylene isomers are used as the unhalogenated aromatic hydrocarbon.

7. The process according to claim 1 wherein the reaction in the first step takes place at a temperature from 20° to 140° C.

8. The process according to claim 1 wherein, in the second step, p-toluenesulfonic acid or its hydrate is used as the acid catalyst.

9. The process according to claim 1 wherein the reaction in the second step takes place at a temperature of from 90° C. to reflux temperature.

10. The process according to claim 1 wherein, in the first and second steps, toluene or xylene isomers are used as the unhalogenated aromatic hydrocarbon.

* * * * *